United States Patent [19]

Smith, Jr. et al.

[11] Patent Number: 4,462,685
[45] Date of Patent: Jul. 31, 1984

[54] SPECTROANALYTICAL SYSTEM

[75] Inventors: Stanley B. Smith, Jr., Westford, Mass.; Gary M. Hieftje, Bloomington, Ind.

[73] Assignee: Instrumentation Laboratory Inc., Lexington, Mass.

[21] Appl. No.: 240,542

[22] Filed: Mar. 4, 1981

[51] Int. Cl.³ .............................................. G01N 21/31
[52] U.S. Cl. ..................................... 356/307; 356/326
[58] Field of Search ............... 356/307, 300, 326, 312, 356/314, 315, 316, 320

[56] References Cited

U.S. PATENT DOCUMENTS

| | | | |
|---|---|---|---|
| 3,089,382 | 7/1957 | Hecht et al. | 356/418 |
| 3,370,503 | 2/1968 | Keahl | 88/14 |
| 3,610,760 | 10/1971 | Lowe | 356/87 |
| 3,689,158 | 9/1972 | Shifrin | 356/87 |
| 3,715,163 | 2/1973 | Mitchell | 356/85 |
| 3,796,499 | 3/1974 | Bonczyk | 356/201 |
| 3,825,344 | 7/1974 | Bonne | 356/85 |
| 3,884,583 | 5/1975 | Kikuchi | 356/201 |
| 3,914,054 | 10/1975 | Hadeishi | 356/51 |
| 3,924,950 | 12/1975 | Siegler, Jr. | 356/82 |
| 3,937,577 | 2/1976 | Dorsch | 356/85 |
| 3,989,983 | 11/1976 | Uchino | 315/248 |
| 4,032,235 | 6/1977 | Kiefer | 356/82 |

FOREIGN PATENT DOCUMENTS 54-25889  2/1979  Japan .................................. 356/307

OTHER PUBLICATIONS

Bath et al., "Sequential Hollow Cathodes for Background Correction in Atomic Absorption Spectrometry", Analytical Chemistry, vol. 50, #11, Sep. 1978, pp. 1597-1599.

Araki, et al., "A Dual Wavelength Atomic Absorption Spectrophotometer Using a Pulsed Hollow Cathode Lamp", Appl. Spectrosc., vol. 31, No. 2, pp. 150-155, (1977).

*Primary Examiner*—F. L. Evans

[57] ABSTRACT

An atomic absorption system comprising a radiation source that emits spectral line radiation characteristic of an element to be analyzed, an analysis region open to passage of the beam of radiation from the source and in which a sample of the substance to be analyzed is atomized, source control means for alternately energizing the source at a first intensity level to provide a radiation output that has a narrow spectral line at a wavelength of an element to be detected and at a higher intensity level to provide a radiation output of broader wavelength with intensity suppression at the wavelength of the narrow spectral line, electronic transducing means for developing an electrical signal corresponding to the sensed radiation intensity of the radiation beam that passes through the analysis region, and a log ratio circuit that utilizes integrated electrical signals corresponding to the two source energization intensity levels to provide background corrected concentration information on the element of interest in the analyzed sample.

11 Claims, 12 Drawing Figures

FIG 1
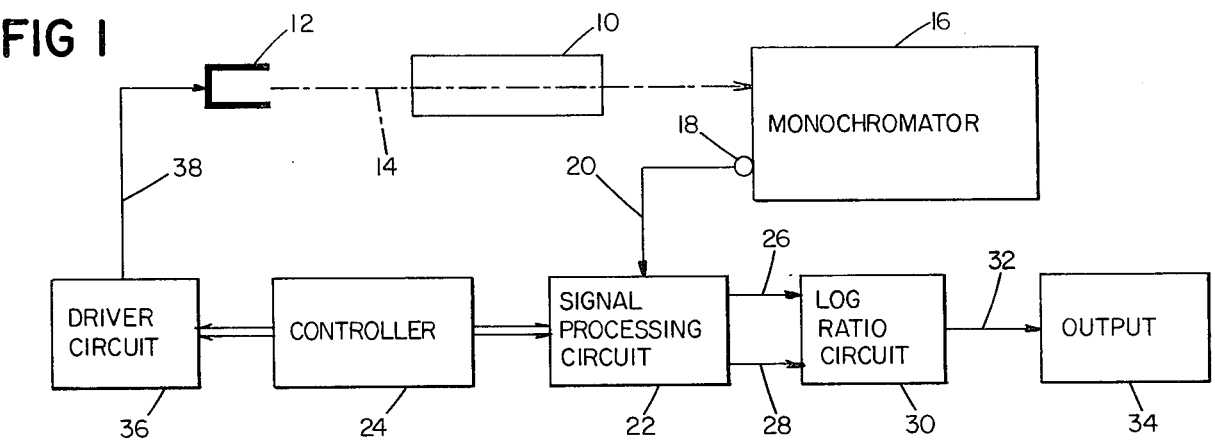
FIG 2
FIG 9
FIG 3
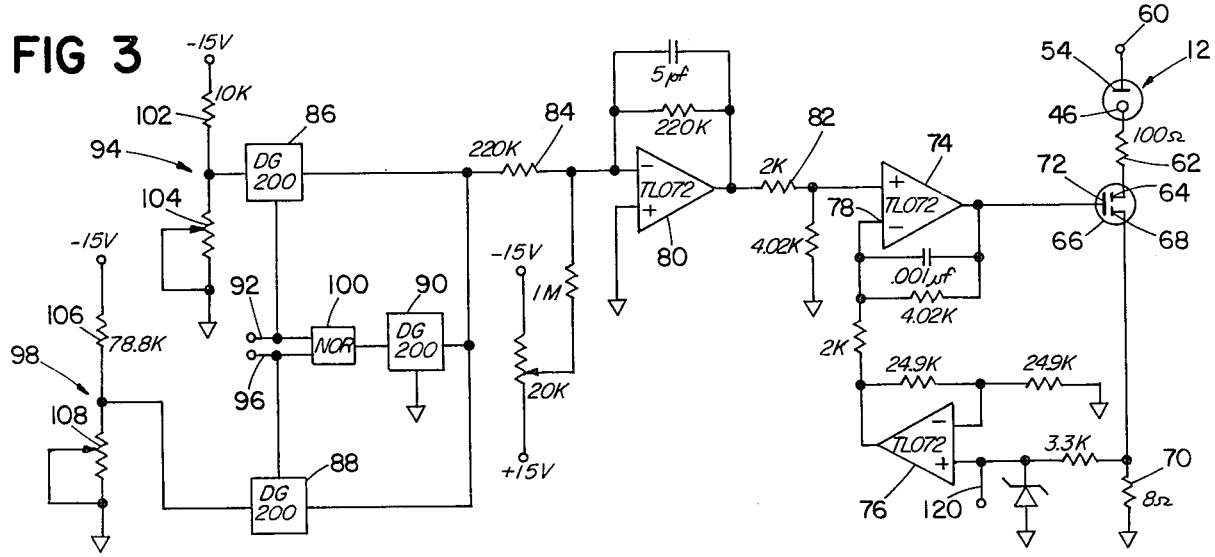
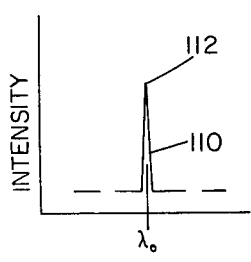
FIG 4A
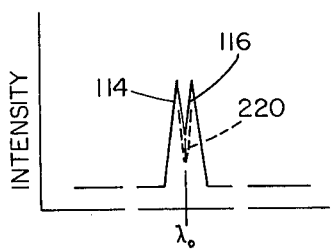
FIG 4B
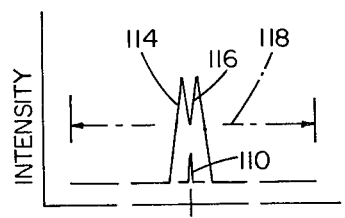
FIG 4C

SPECTROANALYTICAL SYSTEM

This invention relates to spectroanalytical systems and more particularly to systems of the atomic absorption type.

In atomic absorption spectroscopy systems, sample material is atomized, as in a flame or in a tubular furnace, radiation containing a spectral line of the element of interest is passed through the atomized sample material, and the absorption of radiation at the particular wavelength of interest is measured. Frequently, the radiation source is of the hollow cathode type and has a cathode that is formed of or contains the element or elements to be detected, and emits a beam consisting of a steady, intense and stable atomic spectrum of the element or elements forming the cathode. That spectrum contains one or more very narrow spectral lines, one of which is selected by a suitable wavelength selection device such as, for example, a grating or prism monochromator.

It has been recognized that other factors commonly termed "background" affect the accuracy of atomic absorption measurements since total absorption (decrease in intensity of the radiation at the selected wavelength) is measured. Contributing to "background", are such factors as absorption due to molecules rather than free atoms, instability of the radiation source, and scattering due to particles within the sample atomization zone.

A number of arrangements have been used to provide background compensation. Double-beam photometric techniques provide compensation for changes in the source and detection systems, but do not provide adequate compensation for other background factors. In some systems, a broad bandwidth auxiliary source such as a deuterium lamp is used to pass a beam through the sample path (and the reference path in a double-beam system). Another compensation system uses a magnet to produce the Zeeman effect—two distinct, orthogonally polarized beams of radiation, one containing a wavelength nearly identical with the wavelength of the emitting source in the absence of the magnetic field and the other containing radiation of two different wavelengths which lie on either side of the wavelength of the first beam. Among the drawbacks of the broad band reference source type of compensation system are introduction of further background problems due to factors such as variation in the reference source and alignment errors, while the Zeeman type of background compensation system introduces location restrictions due to the magnet, is complex and requires elaborate instrumention.

In accordance with the invention there is provided a spectroanalytical system comprising a radiation source that emits spectral line radiation characteristic of an element to be analyzed, an analysis region open to passage of the beam of radiation from the source and in which a sample of the substance to be analyzed is atomized, source control means for alternately energizing the source at a first intensity level to provide a radiation output that has a narrow spectral line at a wavelength of an element to be detected and at a higher intensity level to provide a radiation output of broader wavelength with intensity suppression at the wavelength of said narrow spectral line, electronic transducing means for developing an electrical signal corresponding to the sensed radiation intensity of the radiation beam that passes through the analysis region, and means for utilizing the relative values of the electrical signals corresponding to the two source energization intensity levels to provide concentration information on the element in the sample analyzed.

In preferred embodiments, the radiation source is a hollow cathode lamp and the system includes first and second electrical signal storage means (e.g., sample and hold circuits), and a synchronous control for alternately storing signals from the transducing means in the two storage means in synchronism with the switching of the intensity levels of the hollow cathode lamp by the source control means. Preferably, the current flow at background correction level is at least five times the current flow at sample intensity level and in a particular system, the current flow through the hollow cathode lamp at the normal (sample) intensity level is in the order of 5–25 milliamperes and at the higher (background correction) intensity level is in the order of 200–500 milliamperes, with a quiescent current level of about one milliampere between the intensity levels. Preferably the system includes means for integrating the electrical signal developed by the transducing means, and the control provides integration intervals inversely related to the intensities of the first and second radiation outputs, the integration interval for the sample signal in a particular embodiment, being sixty times the integration interval from the background correction signal. It will be understood that other integration intervals and source energization levels may be employed depending on the nature of the source and the type of signal processing employed.

In one particular embodiment, a single hollow cathode lamp is used while in another embodiment, an auxiliary unit is employed with the hollow cathode lamp to further suppress the intensity of radiation at the wavelength of the narrow spectral line.

Other features and advantages will be seen as the following description of particular embodiments progresses, in conjunction with the drawings, in which:

FIG. 1 is a block diagram of an atomic absorption spectroanalytical system in accordance with the invention;

FIG. 2 is a perspective view of a radiation source used in the system shown in FIG. 1;

FIG. 3 is a schematic diagram of source driver circuitry used in the system shown in FIG. 1;

FIG. 4 is a series of idealized wavelength intensity plots of outputs of the radiation source in the system of FIG. 1;

FIG. 9 is a perspective view of a supplemental wavelength spectral line suppression device for use in another atomic absorption spectroanalytical system in accordance with the invention.

DESCRIPTION OF PARTICULAR EMBODIMENTS

Figure 5A:
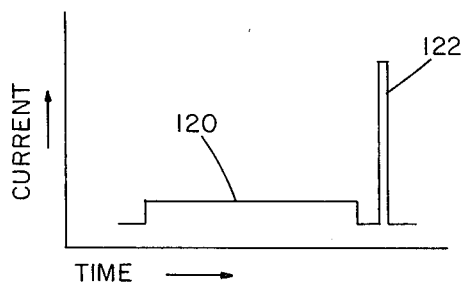
FIGS. 5A and 5B are graphs indicating two different operating modes in accordance with the invention.

With reference to FIG. 1, the atomic absorption analytical system shown in that figure employs structure 10 that defines an analysis region—for example, flame from an atomizing burner into which the sample to be analyzed is aspirated or a tubular atomizing furnace. Radiation source 12 is a hollow cathode lamp that has a cathode of the element or elements to be analyzed and directs a beam 14 of radiation through an atomic vapor in analysis region 10 to a wavelength filter or selector device 16 which is a monochromator in this embodiment. Wavelength selector 16 has photosensor 18 (e.g., a photomultiplier tube) which generates an electrical signal proportional to sensed radiation intensity which is transmitted over line 20 to signal processing circuit 22. Circuit 22 processes that photosensor signal in response to signals from controller 24 and produces outputs over line 26 and 28 that are applied to log ratio circuit 30. The output of circuit 30 is applied over line 32 as an absorbance signal to appropriate output equipment 34 such as a display or a recorder. Controller 24 also applies control signals to driver circuit 36 which applies energizing signals to radiation source 12 over line 38.

Hollow cathode lamp 12, as shown in FIG. 2, includes envelope 40 that has output window 42 through which radiation beam 14 passes and a mounting base 44. Disposed within envelope 40 is a hollow cathode 46 that is supported by insulators 48, 50 and is connected to terminal 52. Cooperating anode 54 is in the form of a ring that is supported on insulator posts 56 and is connected to terminal 58.

Details of hollow cathode drive circuit 36 may be seen with reference to FIG. 3. Hollow cathode lamp 12 has its anode 54 connected to a 400-volt power supply at terminal 60 and its cathode 46 connected through resistor 62 to drain electrode 64 of 450 volt N channel MOSFET electronic switch 66 (Air National Rectifier Model 433). Source electrode 68 is connected to ground through resistor 70 and gate electrode 72 is connected to amplifier stage 74. A feedback loop that includes amplifier 76 is connected between source electrode 68 and the inverting input 78 of amplifier 74. The output of a preamplifier stage 80 is connected via resistor 82 to amplifier 74, and the input to preamplifier 80 via resistor 84 is controlled by electronic selector switches 86, 88, and 90. A signal on control input 92 closes switch 86 to connect voltage divider network 94 to preamplifier 80; a signal on control input 96 closes switch 88 to connect voltage divider network 98 to amplifier 80; and in the absence of a control signal on either line 92 or 96, NOR circuit 100 closes switch 90 to ground the input to amplifier 80. Voltage divider network 94 includes resistor 102 and potentiometer 104 and its output via selector switch 86 provides a first intensity level energization of hollow cathode lamp 12. Network 98 includes resistor 106 and potentiometer 108 and its output via switch 88 energizes hollow cathode lamp at a second and higher intensity level.

In a first or sample mode, switch 86 is closed and the signal from divider network 94 is applied through amplifiers 80 and 74 to turn on switch 66 to provide sample current ($i_S$) flow through hollow cathode lamp 12. The output waveform 110 of source 12, as indicated in FIG. 4A in this first or sample energization mode has a narrow spectral line form with a peak 112 at wavelength $\lambda_0$. In a second or background mode, switch 88 is closed and a signal from divider network 98 is applied through amplifiers 80 and 74 to operate switch 66 so that a much higher current ($i_B$) flows through hollow cathode lamp 12, a current flow of 300 milliamperes producing an output waveform 114 as indicated in FIG. 4B, that waveform having reduced or suppressed intensity at wavelength $\lambda_0$ as indicated at 116. The half width of sample intensity waveform 110 is about 0.005 angstrom while the half width of broadened background correction waveform 114 is about 0.02 angstrom, its width varying from element to element. Monochromator 16 has a slit width (band pass) of about five angstroms as indicated at 118 in FIG. 4C. The two intensity curves are superimposed in FIG. 4C, the total area of the high (background correction) intensity waveform 114 being about 60 times the area of sample intensity waveform 110.

Figure 5B:
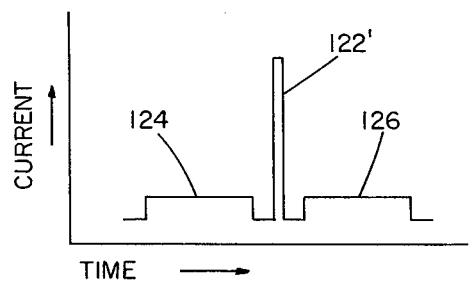

In operation, source 12 is alternately energized by driver circuit 36 in normal (sample) intensity mode (FIG. 4A) and in high (background) intensity mode (FIG. 4B). The duration of the normal intensity mode energization nominally being twelve milliseconds (but variable by controller 24), and the duration of each high intensity mode energization nominally being 300 microseconds. The graph of FIG. 5A shows an operating sequence in which source 12 is energized in normal ($i_S$) intensity mode 120 for twelve milliseconds at a current that is typically less than 20 milliamperes but may be 50 milliamperes or higher; and then in background correction mode 122 for 300 microseconds with an intensity that is typically at least 200 milliamperes. The output from source 12 is integrated in each mode (with allowance of 100 microseconds for settling time) so that the integration time in sample intensity mode 120 is approximately sixty times the integration time in background intensity mode 122. The integrated signals are stored in separate sample and hold circuits and then ratioed to provide a corrected absorbance signal. FIG. 5B is a similar graphical representation of another sequence of system operation (particularly useful in analyzers that employ an atomizer of the tubular furnace type), in which source 12 is first energized for six milliseconds in sample intensity mode 124, then energized for 300 microseconds in high intensity mode 122', and then energized for another six milliseconds in sample intensity mode 126, again providing an integration time ratio of about 60.

Figure 6:
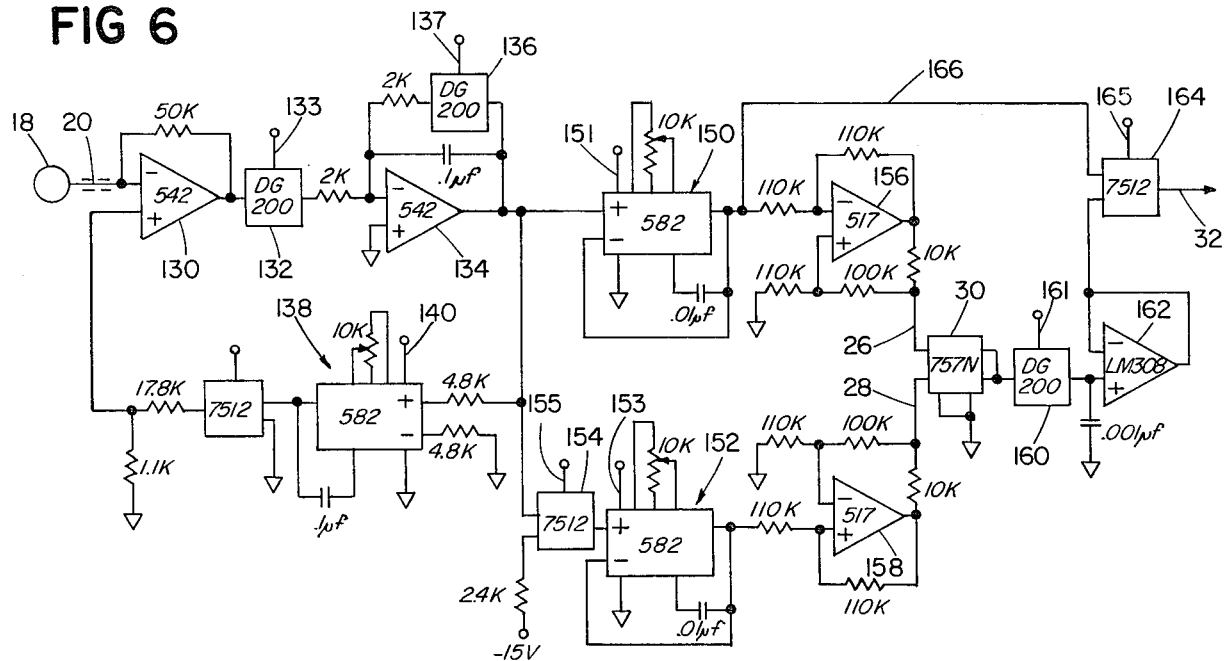
FIG. 6 is a schematic diagram of signal processing circuitry employed in the system shown in FIG. 1.

Details of signal processing circuit 22 may be seen with reference to FIG. 6. That figure shows a single channel processing circuit, but it will be apparent that similar circuitry may be utilized in dual channel systems as well as in double beam systems. Processing circuit 22 includes preamplifier stage 130 whose output is connected via switch 132 to integrator circuit 134 that functions as a filter when switch 136 is closed. When a control signal is applied on line 140, DC restore loop 138 is connected from the output of integrator 134 to the input of preamplifer 130.

Connected to the output of integrator 134 are two sample and hold circuits 150, 152, circuit 150 being connected directly to integrator 134 and circuit 152 being connected through switch 154 that disconnects circuit 152 from integrator 134 and connects a reference voltage to circuit 152 in response to a signal on control input 155 when the system is to be used without background correction. The output of sample and hold circuit 150 is connected via amplifier 156 and input line 26 to log ratio circuit 30, and the output of sample and hold circuit 152 is connected via amplifier 158 and input line 28 to log ratio circuit 30. Connected to the output of log ratio circuit 30 via electronic switch 160 (that is closed when control input 161 is energized) is driver amplifier 162 and electronic switch 164 which provides an absorbance output on line 32. In an alternate (emission) mode of operation, the sample signal from circuit 150 may be applied over line 166 through switch 164 directly to output line 32.

Figure 7:
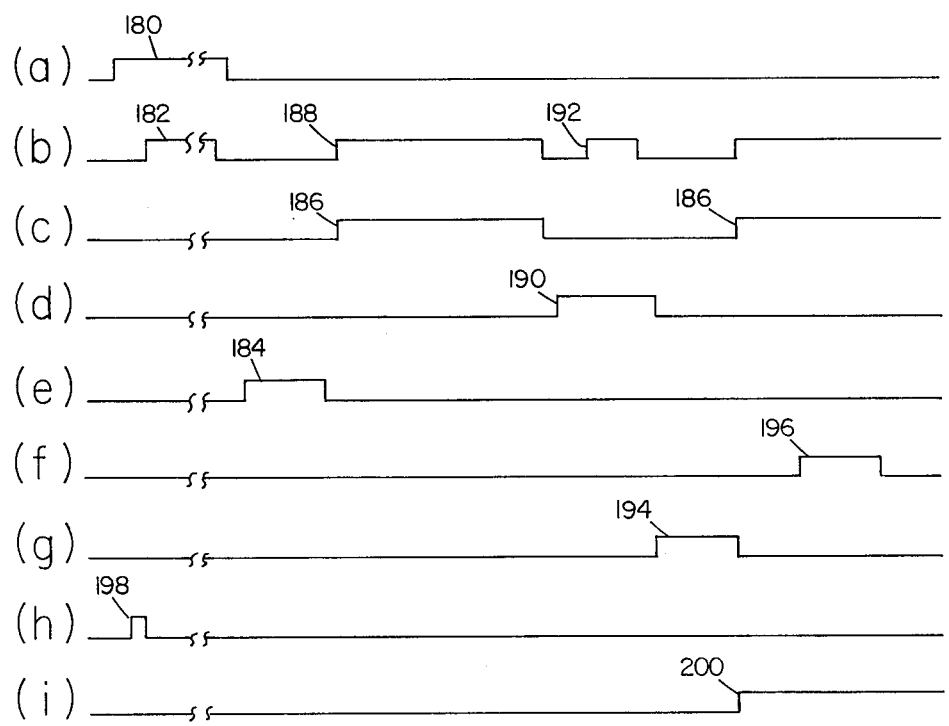
FIG. 7 is a timing diagram illustrating an operating sequence of the system shown in FIG. 1.

Further understanding of the operation of the system shown in FIG. 1 may be had with reference to the timing diagram of FIG. 7. That indicates a sequence of control signals that are generated by controller 24 and applied to signal processing circuit 22 and driver circuit 36. Pulse 180 is applied over line 92 to close switch 86; pulses 182, 188 and 192 are applied over line 133 to close switch 132; pulses 186 are applied on line 137 to close switch 136 and reset integrator 134; pulse 190 is applied on line 96 to close switch 88; pulse 184 is applied over line 151 to sample and hold circuit 150; pulse 194 is applied over line 153 to sample and hold circuit 152; pulse 196 is applied over line 161 as an I-O update pulse; pulse 198 is a reset signal generated at the beginning of each analysis cycle; pulse 200 is a DC restore signal that is applied over line 140 to circuit 138.

With reference to FIG. 3, hollow cathode lamp 12 is energized by pulse 180 in its sample mode (typically less than a 20 milliampere current level) for a time interval that is variable in one millisecond intervals by controller 24. Integration pulse 182 starts 100 microseconds after sample pulse 180 and terminates ten microseconds before pulse 180 terminates so that the signal from photosensor 18 is passed by amplifier 130 to integrator 134 (FIG. 5). Thus integrator 134 accumulates the output signal of photosensor 18 for the time duration interval determined by pulse 182. Pulse 184 of 300 microseconds duration then energizes line 151 to transfer the integrated signal from integrator 134 to sample and hold circuit 150. An integrator reset signal 186 on line 137 discharges the capacitor in integrator 134 and switch 132 is closed (pulse 188 of 1000 microseconds duration) so that signal from photosensor 18 is passed with circuit 134 in its filter mode. At the end of pulse 188, pulse 190 (of 310 microseconds duration) is applied on line 96 to close switch 88 and energize hollow cathode lamp 12 in its high intensity mode, typically with a current of 200 or more milliamperes, to produce an output as indicated in FIG. 4B; 100 microseconds later pulse 192 connects integrator 134 to photosensor 18 to accumulate the output of photosensor 18 for 200 microseconds; ten microseconds later pulse 194 (of 300 microseconds duration) energizes line 153 to transfer the charge from integrator 134 to sample and hold circuit 152. The two signals stored in sample and hold circuits 150 and 152 are applied through amplifiers 156, 158 to log ratio circuit 30. When I-O update pulse 196 is applied on line 161 to close switch 160, the output of ratio circuit 30 is applied through amplifier 162 to output line 32 as a background corrected absorbance output which is used or displayed as desired. DC restore signal 200 generated at the end of the analysis cycle on line 140 completes feedback loop 138 in preparation for the next analysis cycle. During intervals between pulses 180 and 190 current flow through tube 12 is at a quiescent level of about 0.5 milliampere.

This background correction system has been evaluated for a number of elements, including those summarized in the following table. Absorbance values were first measured with the normal ($i_S$) current to hollow cathode lamp 12 and then absorbance values were measured with the background correction ($i_B$) current to lamp 12. The resulting percent reduction in absorbance is set out in Table 1 under the heading "Modulation Depth".

TABLE 1

| Element | $i_S$ | $i_B$ | Modulation Depth |
|---|---|---|---|
| Ag | 8 | 200 | 85 |
| Al | 16 | 300 | 27 |
| As | 18 | 400 | 54 |
| Au | 12 | 200 | 54 |
| Ba | 12 | 300 | 25 |
| Be | 8 | 200 | 59 |
| Cd | 8 | 200 | 94 |
| Co | 14 | 400 | 79 |
| Cu | 10 | 300 | 70 |
| Cr | 16 | 400 | 51 |
| Fe | 14 | 300 | 50 |
| Pb | 8 | 300 | 78 |
| Mn | 8 | 300 | 68 |
| Ni | 8 | 300 | 78 |
| Pt | 12 | 300 | 40 |
| Se | 16 | 300 | 49 |
| Tl | 8 | 300 | 48 |
| Sn | 8 | 300 | 47 |
| V | 12 | 400 | 28 |
| Zn | 8 | 300 | 91 |

Figure 8:
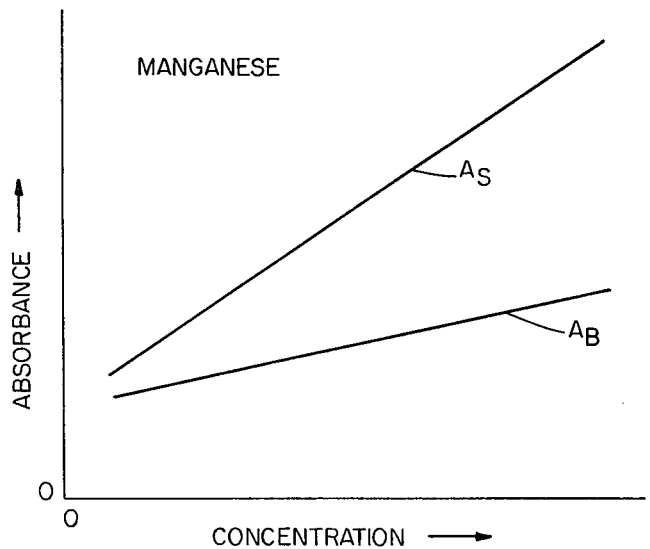
FIG. 8 is a graphical showing of absorbance data obtained with the system shown in FIG. 1.

Where:
$i_S$ = Sample peak current, mA
$i_B$ = Background peak current, mA
Modulation Depth = $\frac{A_S - A_B}{A_S} \times 100$
$A_S$ = Absorbance during sample pulse
$A_B$ = Absorbance during background pulse The curve in FIG. 8 illustrates the nature of background correction obtained with this system on the element manganese (a "modulation depth" of 68 percent).

Further intensity suppression of valley 116 in the high intensity mode (FIG. 4B) may be achieved with the auxiliary unit 200 shown in FIG. 9. That unit is inserted in radiation beam 14 between source 12 and analysis cell 10 (FIG. 1). As indicated in FIG. 9, unit 200 includes an envelope 202 with planar quartz windows 204, 206 at opposite ends. Ceramic disc 208 supports cathode 210 that includes the same element or elements to be analyzed as lamp 12 and has a cylindrical through passage 212. Auxiliary unit 200 is mounted so that radiation beam 14 is directed through passage 212 with a lens (not shown) between quartz windows 42 and 204 focusing cathode 46 on cathode passage 212. Cathode cylinder 210 is energized via terminal connection 218. In use, unit 200 is energized concurrently with energization of source 12 in its high current mode. Atoms of the element to be detected are generated in passage 212 and absorb radiation in beam 14, producing supplemental reduction in the valley 116—as indicated at 220 in FIG. 4B.

While particular embodiments of the invention have been shown and described, various modifications thereof will be apparent to those skilled in the art and therefore it is not intended that the invention be limited to the disclosed embodiments or to details thereof and departures may be made therefrom within the spirit and scope of the invention.

What is claimed is:

1. A spectroanalytical system comprising a radiation source that emits spectral line radiation characteristic of an element to be analyzed, an analysis region open to passage of the beam of radiation from the source and in which a sample of the substance to be analyzed is atomized, source control means including an electronic switch for controlling current flow to said radiation source, first current level establishing means, second current level establishing means, quiescent current level establishing means, and means for alternately connecting said first and second current level establishing means in circuit with said electronic switch to energize said source at a first intensity level when said first current level energizing means is connected to said electronic switch to provide a first narrow spectral line radiation output that has a spectral line peak at a wavelength of an element to be detected, and to energize said source at a second higher intensity level when said second current level establishing means is connected to said electronic switch to provide a second radiation output of broader wavelength with partial suppression of intensity at the center wavelength of said first radiation output, said alternate connections of said first and second current level establishing means being spaced in time so that said quiescent current level establishing means energizes said source at a quiescent current level of about one milliampere during the intervals between said first and second intensity levels, said source and said analysis region being arranged such that radiation from said source is passed directly from said source into said analysis region without further central wavelength intensity suppression, electronic transducing means for developing an electrical signal corresponding to the sensed radiation intensity of the radiation beam from said source that passes through said analysis region, and means for utilizing the relative values of said electrical signals corresponding to said first and second radiation outputs to provide concentration information on said element in the sample analyzed.

2. The system of claim 1 wherein said radiation source comprises a hollow cathode lamp.

3. The system of either claim 1 or 2 wherein the depth of said intensity suppression of said second radiation output as it passes into said analysis region is in the range of 25-95%.

4. The system of claim 2 wherein each said current level establishing means includes a voltage divider network.

5. The system of claim claim 2 wherein said second current level estblishing means energizees said lamp at a current level that is at least five times the lamp energizing current level provided by said first current level establishing means.

6. The system of either claim 1 or 2 and further including an integrator, first and second electrical signal storage means, a synchronous control connected in circuit between said transducing means and said integrator for applying output signals from said transducing means to said integrator during time intervals corresponding to the time interval that current is being applied to said radiation source by said first and second current level establishing means, each said corresponding time interval during which said synchronous control is applying signals from said transducer to said integrator commencing after and terminating before the time interval that current is being applied to said radiation source by said current level establishing means, and further electronic switch means for alternately storing signals from said integrator in said first and second storage means in synchronism with the switching of the intensity levels of said source by said source control means, and wherein said utilizing means employs the ratio of said stored signals to provide said concentration information.

7. The system of claim 6 wherein said utilizing means includes a log ratio amplifier.

8. The system of claim 7 and further including means for bypassing said log ratio amplifier for operating said spectroanalytical system in emission mode; and means for imposing a fixed reference signal on said log ratio amplifier for operating said system in absorption mode without background correction.

9. The system of claim 6 wherein said synchronous control provides integration intervals inversely related to the intensities of said first and second radiation outputs.

10. The system of claim 6 wherein each said current level establishing means includes a voltage divider network.

11. An atomic absorption system comprising a hollow cathode lamp that emits spectral line radiation characteristic of an element to be analyzed, an analysis region open to passage of the beam of radiation from said lamp and in which a sample of the substance to be analyzed is atomized, lamp control means including an electronic switch for controlling current flow to said lamp, first current level establishing means, second current level establishing means, quiescent current level establishing means, and means for alternately connecting said first and second current level establishing means in circuit with said electronic switch to energize said lamp at a first intensity level when said first current level energizing means is connected to said electronic switch to provide a first narrow spectral line radiation output that has a spectral line peak at a wavelength of an element to be detected, and to energize said lamp at a second higher intensity level when said second current level establishing means is connected to said electronic switch to provide a second radiation output of broader wavelength with partial suppression of intensity at the center wavelength of said first radiation output, said alternate connections of said first and second current level establishing means being spaced in time so that said quiescent current level establishing means energizes said lamp at a quiescent current level of about one milliampere during the interval between said first and second intensity levels, said lamp and said analysis region being arranged such that radiation from said lamp is passed directly from said lamp into said analysis region without further central wavelength intensity suppression, a monochromator for isolating a relatively narrow region containing said central wavelength, electronic transducing means coupled to said monochromator for developing an electrical signal corresponding to the sensed radiation intensity of the radiation beam from said lamp that passes through said analysis region, means for integrating the electrical signal developed by said electronic transducing means, control means providing integration intervals inversely related to the intensities of said first and second radiation outputs, first and second electrical signal storage means, a synchronous control for alternately storing signals from said integrating means in said first and second storage means in synchronism with the switching of the intensity levels of said lamp by said lamp control means, and means responsive to the ratio of said stored signals to provide background corrected concentration information on said element in the analyzed sample.

* * * * *